United States Patent
Buchmann et al.

(10) Patent No.: US 6,322,754 B1
(45) Date of Patent: Nov. 27, 2001

(54) TRANSLATABLE HOOD ARRANGEMENT FOR A MEDICAL-TECHNICAL OR DENTAL-TECHNICAL WORKTABLE

(75) Inventors: Siegfried Buchmann, Aitrach; Günther Weiss, Leutkirch, both of (DE)

(73) Assignee: Kaltenbach & Voigt GmbH & Co., Biberach (DE)

( * ) Notice: Subject to any disclaimer, the term of this patent is extended or adjusted under 35 U.S.C. 154(b) by 0 days.

(21) Appl. No.: 09/231,199

(22) Filed: Jan. 14, 1999

(30) Foreign Application Priority Data

Jan. 15, 1998 (DE) .............................. 198 01 316

(51) Int. Cl.⁷ .................................................. B08B 15/02
(52) U.S. Cl. ........................ 422/104; 422/99; 422/101; 454/49; 454/56; 454/63; 454/65; 210/244
(58) Field of Search ........................... 422/9.9, 101, 104; 454/49, 56, 63, 65; 210/244; 108/50.11, 90, 50

(56) References Cited

U.S. PATENT DOCUMENTS

| | | | |
|---|---|---|---|
| 4,227,902 | * | 10/1980 | Olson .................................. 55/302 |
| 4,596,060 | * | 6/1986 | Schmidt et al. ................... 15/312 R |
| 4,607,416 | * | 8/1986 | Schmidt et al. ....................... 15/301 |
| 4,653,715 | * | 3/1987 | Schmidt et al. ................... 248/281.1 |
| 5,133,691 | * | 7/1992 | Karlsson ............................... 454/56 |
| 5,641,191 | * | 6/1997 | Jia ..................................... 276/97.6 |
| 5,743,503 | * | 4/1998 | Voeller et al. ..................... 248/284.1 |
| 5,791,260 | * | 8/1998 | Mack et al. ........................ 108/50.11 |
| 5,928,075 | * | 7/1999 | Miya et al. ............................. 454/56 |

FOREIGN PATENT DOCUMENTS

| | | |
|---|---|---|
| 33 39 658 C1 | 8/1985 | (DE) . |
| 35 43 602 A1 | 7/1986 | (DE) . |
| 195 06 966 A1 | 10/1995 | (DE) . |
| 196 24 506 A1 | 3/1997 | (DE) . |
| 19801315 | * 7/1999 | (DE) . |
| 598246 | * 5/1994 | (EP) . |
| 749710 | * 12/1996 | (EP) . |
| 930055 | * 7/1999 | (EP) . |

* cited by examiner

Primary Examiner—Jill Warden
Assistant Examiner—Kathryn Bex
(74) Attorney, Agent, or Firm—Scully, Scott, Murphy & Presser

(57) ABSTRACT

The invention relates to a medical-technical or dental-technical work table (1) which in its forward region of its table surface (2a) has a protection arrangement (11) having a protection plate (11c) in upwardly extending arrangement, which protection plate is held on the work table by means of a holder (12), whereby there is provided a rearward rear-wall-like protection arrangement part (11b) having a rear wall (11d; 52) behind the protection plate (11c) which part is positionable in a disposition on the work table (1) and/or on a carrier arm (14) in which the rearward protection arrangement part (11b) forms with the protection plate (11c) a hood-shaped protection arrangement (11).

9 Claims, 5 Drawing Sheets

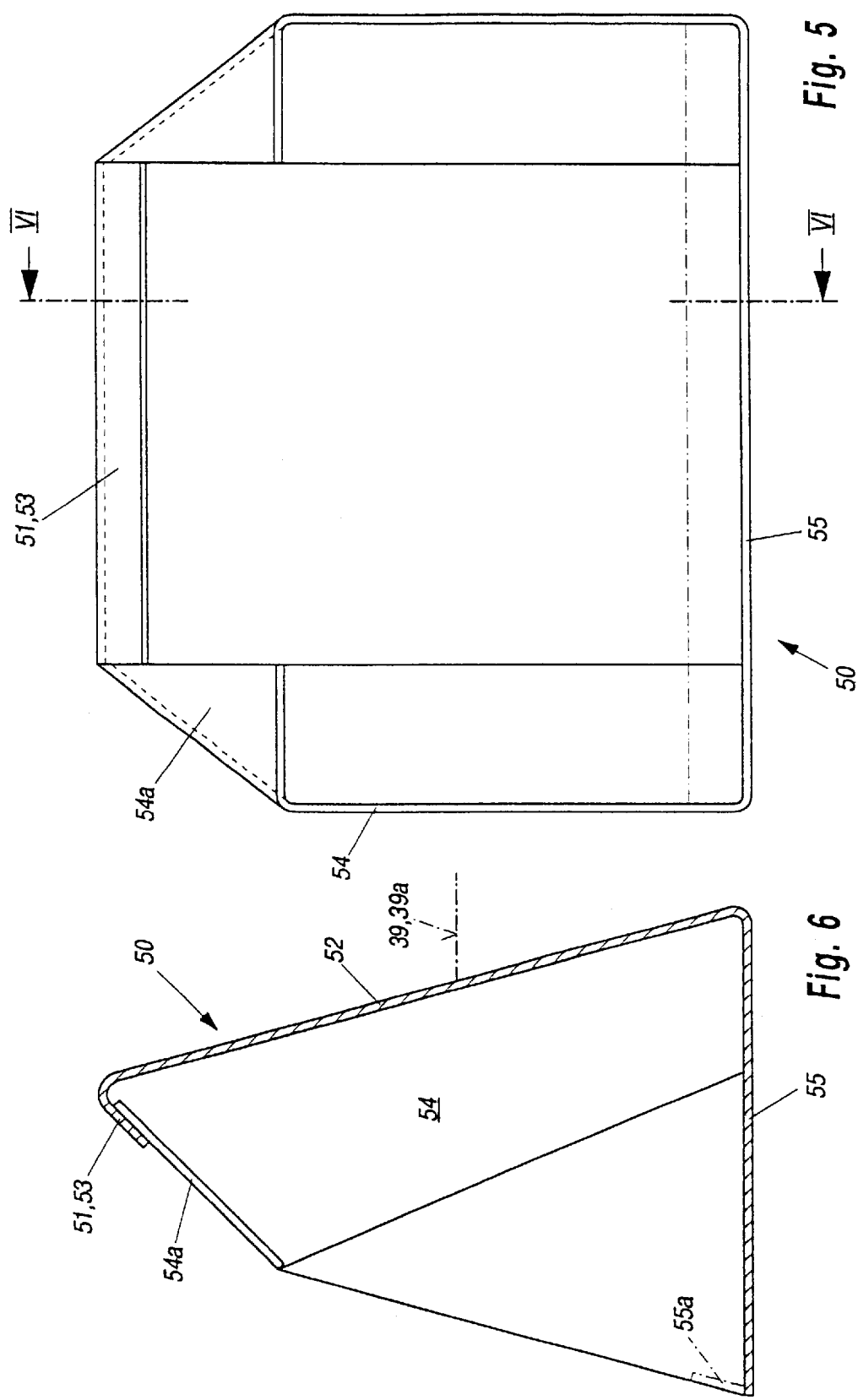

TRANSLATABLE HOOD ARRANGEMENT FOR A MEDICAL-TECHNICAL OR DENTAL-TECHNICAL WORKTABLE

BACKGROUND OF THE INVENTION

1. Field of the Invention

The invention relates to a medical-technical or dental-technical work table which has a protection arrangement in the forward region of the table surface.

Such a work table is employed in a medical-technical or dental-technical laboratory, or also in medical or dental practices, in order to be able to carry out various kinds of work in a readily manipulable manner and with quality. Here, there may be involved e.g. material removing processing measures on a workpiece or model, or testing measures such as technical measurement procedures or optical examinations.

2. Discussion of the Prior Art

With a known work table for a medical- or dental-technical laboratory, described in DE 196 24 506 A1, there is provided a hood-like protection arrangement having a forward protection plate of transparent material, which is intended to protect the user from injury through chips resulting from processing in the case of material-removing processings to be carried out in the region of the protection arrangement, or also from the spreading of dust arising in the processing.

FIG. 2 of this publication shows a hood-shaped protection arrangement having a forward, transparent protection plate and a rearward protection wall, which are both held at the forward end of a carrier arm extending from the rear forwardly.

FIG. 9 of this publication shows a medical- or dental-technical work table in accordance with the state-of-the-art, with which there is present a protection arrangement formed only by means of a transparent forward plate, whereby the plate is attached, in a rearwardly obliquely upwardly extending arrangement, at its lower edge region to an attachment limb extending upwardly from the work table. This protection arrangement affords no protection function to the rear.

SUMMARY OF THE INVENTION

The object of the present invention is to so configure a medical-technical or dental-technical work table of the kind indicated in the introduction that whilst ensuring a simple configuration and/or arrangement the protection of the protection device is extended to the rear.

With the work table according to the invention in accordance with one embodiment, the protection arrangement has additionally to the protection plate a rearward protective wall-like protection arrangement part which at its upper edge forms with the protection plate a hood-like protection arrangement and preferably abuts directly or indirectly on the protection plate and thereby extends its protection not only forwardly but at least in the upper part region also to the rear. By these means, the rear part of the work table is at least partially protected from contaminants resulting from the processing. Thereby, the rearward protection arrangement part can be positioned on the work table preferably so that it abuts with its upper edge on the protection plate in a stable disposition and/or it may be retained at a carrier arm preferably so that it abuts in its upper edge region on the protection plate, whereby in both cases a hood-like construction is afforded. Within the scope of the invention, however, the rearward protection arrangement part may also, when it is retained at a carrier arm, stand up on the work table surface. It is also possible and advantageous to use a carrier arm which can be positioned into any arbitrary height position and which remains in place, so that the rearward protection arrangement part is capable also in a position raised from the work table surface of fulfilling the hood-like arrangement with the protection plate. For this purpose, the carrier arm may have a weight compensation device, or be fixable in the respective adjusted position.

With the configuration according to the invention in accordance with another embodiment, the rearward protection arrangement part is adapted to the protection plate and thereby held at the upper end region of the protection plate or arranged standing up on the table surface, so that it does not need a carrier arm for the positioning of the rearward protection arrangement part. Within the scope of the invention, the rearward protection arrangement part may be arranged hanging on the protection plate and/or it may also extend as far as the work table surface and stand on this surface.

With both configurations in accordance with the invention the forward and rearward protection arrangement parts compliment one another to form a common hood-like protection arrangement, whereby the rearward protection arrangement part has the opening for observation and the forward protection arrangement part has the protection plate for the closing of the opening. Thereby the configurations in accordance with the invention distinguish themselves by a simple manner of construction. With the configuration according to the first embodiment, this is provided in that the rearward protection arrangement part is a separate component which can be manufactured simply and in a cost favourable manner, whereby its positioning can be ensured by means of standing up on the work table surface or by means of the carrier arm likewise in simple manner.

As a result of the simple arrangements and configurations, the features in accordance with the invention can also be manufactured easily and in a cost favourable manner and can install or position the rearward protection arrangement part on the work table. A further advantage of the configuration in accordance with the invention consists in that the rearward protection arrangement part can be readily manipulably and rapidly be brought into working disposition, and again removed. By these means, the work table can be adapted simply and rapidly to various kinds of work, e.g. to work with different degrees of contamination, which enhances the usability of the work table.

Features are contained in the subclaims which lead to simple, compact, cost-favourably manufacturable and reliable constructions, whereby various features also make possible a collection of contaminant particles in the rearward protection arrangement part and thereby contribute to the cleanliness of the work table.

BRIEF DESCRIPTION OF THE DRAWINGS

Below, the invention and further advantages which can be achieved thereby will be described in more detail with reference to exemplary embodiments and to the drawings, which show:

FIG. 5 a rearward protection arrangement part in a view from the front;

FIG. 6 the section VI—VI of FIG. 5.

BRIEF DESCRIPTION OF PREFERRED EMBODIMENTS

Figure 1:
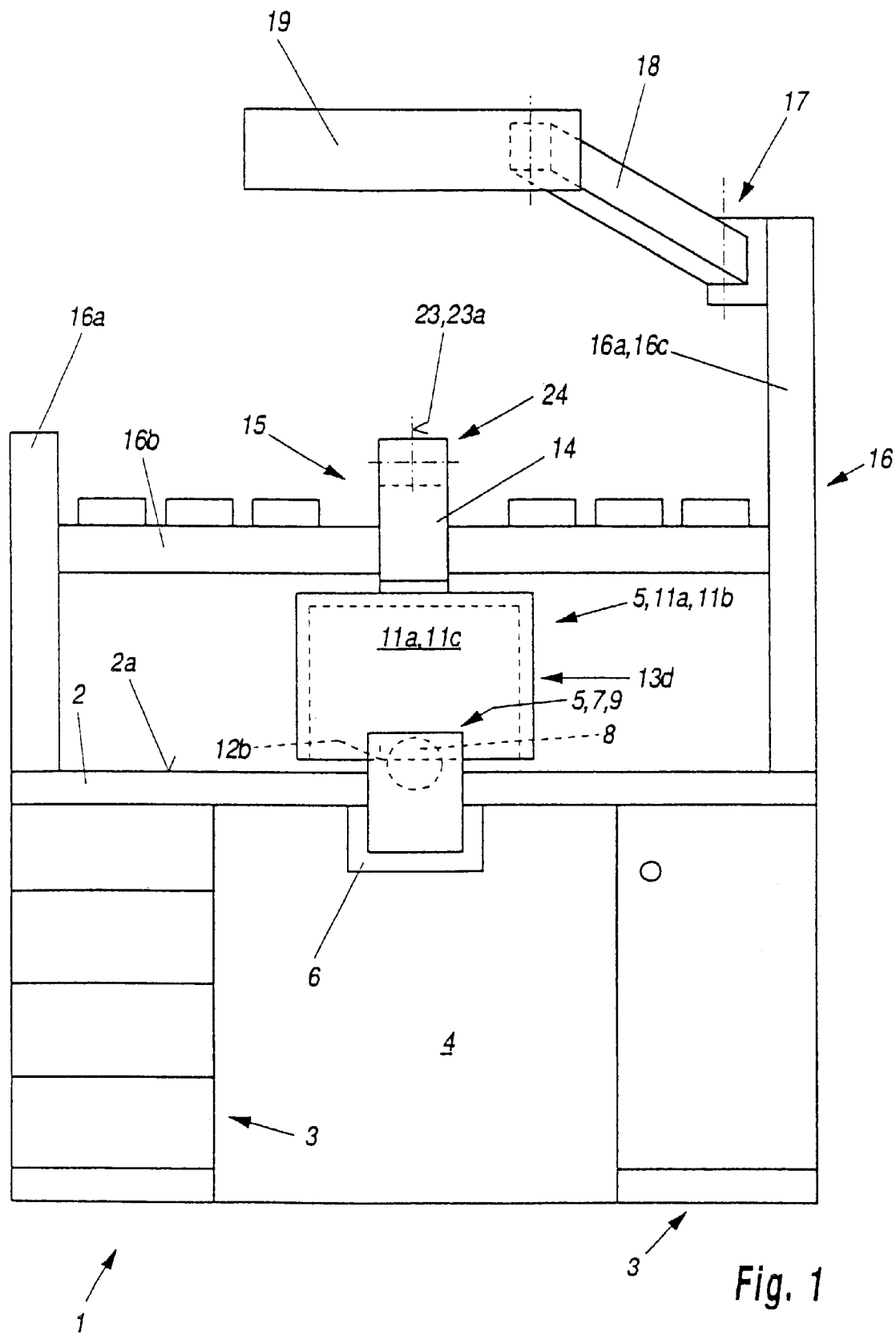
FIG. 1 a medical-technical or dental-technical work table in a view from the front.

The work table, generally indicated by 1, is suitable in particular for dental-technical purposes, but it can however also be used for general medical-technical purposes. The work table 1 consists of a table plate 2 having an upper table surface 2a and two lateral, block-shaped table legs 3 arranged continuously from the front to the rear, in which drawers or cupboards accessible from the front are arranged and between which there is present a free space 4 for the legs of the person (not shown) sitting at the operating side at the work table 1. Further, the work table has a plurality of working devices, of which one working device 5 is preferably moveable in an associated guide 6 between a non-use position pushed back under the table plate 2 and a use position pushed forward in the forward region on the table plate 2. Here, there is involved a suction device 7 having a rearwardly or upwardly emerging suction opening 8, in the region of which—here to the rear—a working position 9 is located on the table surface 2a or on a base plate of the working device 5 or of the suction device 7.

The working position 9 has associated with it a further working device 5 in the form of a protection arrangement 11 the purpose of which is to protect the surroundings in particular forwardly and also rearwardly from contamination originating from the working position 9 in working operation. Here, there may be involved chips or dust resulting from a material-removing processing.

The protection arrangement 11 consists of a forward protection arrangement part 11a and a rearward protection arrangement part 11b. The forward protection arrangement part 11a has a transparent flat front plate 11c, which has a rectangular or quadratic shape and is retained at its lower edge region in a holder 12, which is attached to the table plate and has an up-standing attachment wall 12a to which the front plate 11c is preferably releasably attached, in particular in a plug-in fitting which may be formed by means of a groove 12b arranged in the plane of the front plate 11c, into which the front plate 11c can be inserted from above with a certain clamping force and is thereby retained.

The rearward protection arrangement part 11b has at least one rear wall which with its upper—preferably straight extending edge—abuts on the front plate 11c in particular in its upper region and thereby forms with the front plate 11c a hood-shaped protection arrangement 11. Preferably, the rear wall extends in the working position of the rearward protection arrangement part 11b downwardly to the table surface 2a.

With the present configuration, the protection arrangement 11 is formed in a box shape, whereby the rearward protection arrangement part 11b and the forward protection arrangement part 11a, in the form of the front plate 11c, complement one another to a box-shape. If applicable, from the rear wall 11d there extends forwardly a horizontal cover wall 11e, the straight and horizontal forward edge of which bounds upwardly an opening 11f, which lies in an opening plane extending rearwardly obliquely upwardly. From the side edges of the rear wall 11d there extend forwardly side walls 11g which are fixedly connected with the cover wall 11e and the upper edges of which likewise develop rearwardly obliquely upwardly and bound the opening 11f in the opening plane. The side walls 11g may extend up to the forward mounting wall 12a, so that a forward end wall is not necessary, but may however be present. In the lower forward regions of the side walls 11g there are arranged access holes 11h which serve for the access of the hands of the operating person and make possible work at the working position 9 in the region of the protective hood 13 forming the protection arrangement 11. The arrangement and shaping is so effected that with the protection hood 13 standing on the table surface 2a the upper edges of the side walls 11g are located in the opening plane and thus the protective hood 13 is in a disposition pushed forwardly against the front plate 11c, the front plate 11c covering over and closing the opening 11f.

The protection arrangement 11 is releasably connected with a carrier arm 14 of a carrier device 15 by means of a first connection device in the form of a quick coupling 14a. The quick coupling 14a has a projecting coupling pin 14b and a coupling recess 14c which receives the coupling pin, which pin and which recess form a plug-in coupling and in the plugged-together position are secured one to another by means of an axial securing device, e.g. a non-illustrated latching arrangement.

The carrier device 15 has a carrier column or a carrier frame which is attached in the rear region of the work table 1, in particular on this table, and extends from this table upwardly. With the configuration in accordance with FIG. 1, there is provided a quadrilateral carrier frame 16 having lateral carrier columns 16a and a horizontal transverse 16b from which the carrier arm 14 extends forwardly. At an upwardly projecting extension 16c, for example of the right carrier column 16a, an approximately horizontal carrier arm 18 is pivotably mounted by means of a joint 17 having a vertical joint axis, which at its forwardly projecting free end is horizontally pivotably connected with a light 19 for the work table 1 by means of a further joint having a vertical joint axis. On the transverse 16b there may be arranged repository locations, e.g. supply containers for tools or parts to be installed, which will be needed for the work on the work table 1.

The coupled-on protection arrangement 11 is, with the aid of the carrier arm 14, moveable back and forth in each of its height disposition and laterally and transversely to the working side 21 of the work table 1 and is preferably fixable in the respective position. For the purpose of setting the height there can serve a non-illustrated weight compensating device, or the vertical joints concerned may be fixable or so stiffly moveable that they can be overcome manually but remain in the respective position. Moveability is served by a base joint 23 having a vertical joint axis 23a and a joint 24 having a horizontal joint axis 24a.

Figure 2:
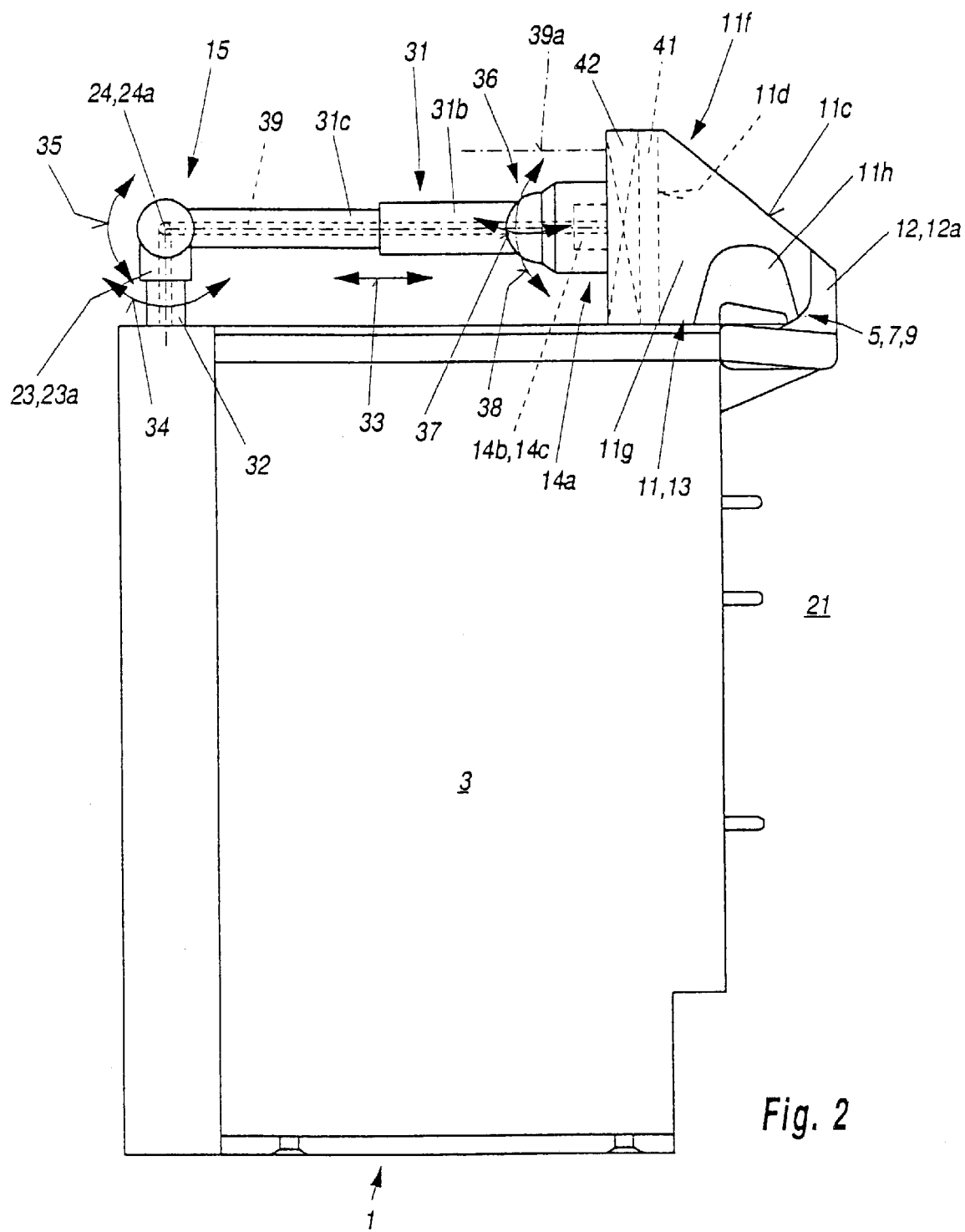
FIG. 2 a medical-technical or dental-technical work table having a carrier arm, extending from the rear forwardly, of a carrier device arranged on the work table, for a protection arrangement, in a side view.
Figure 3:
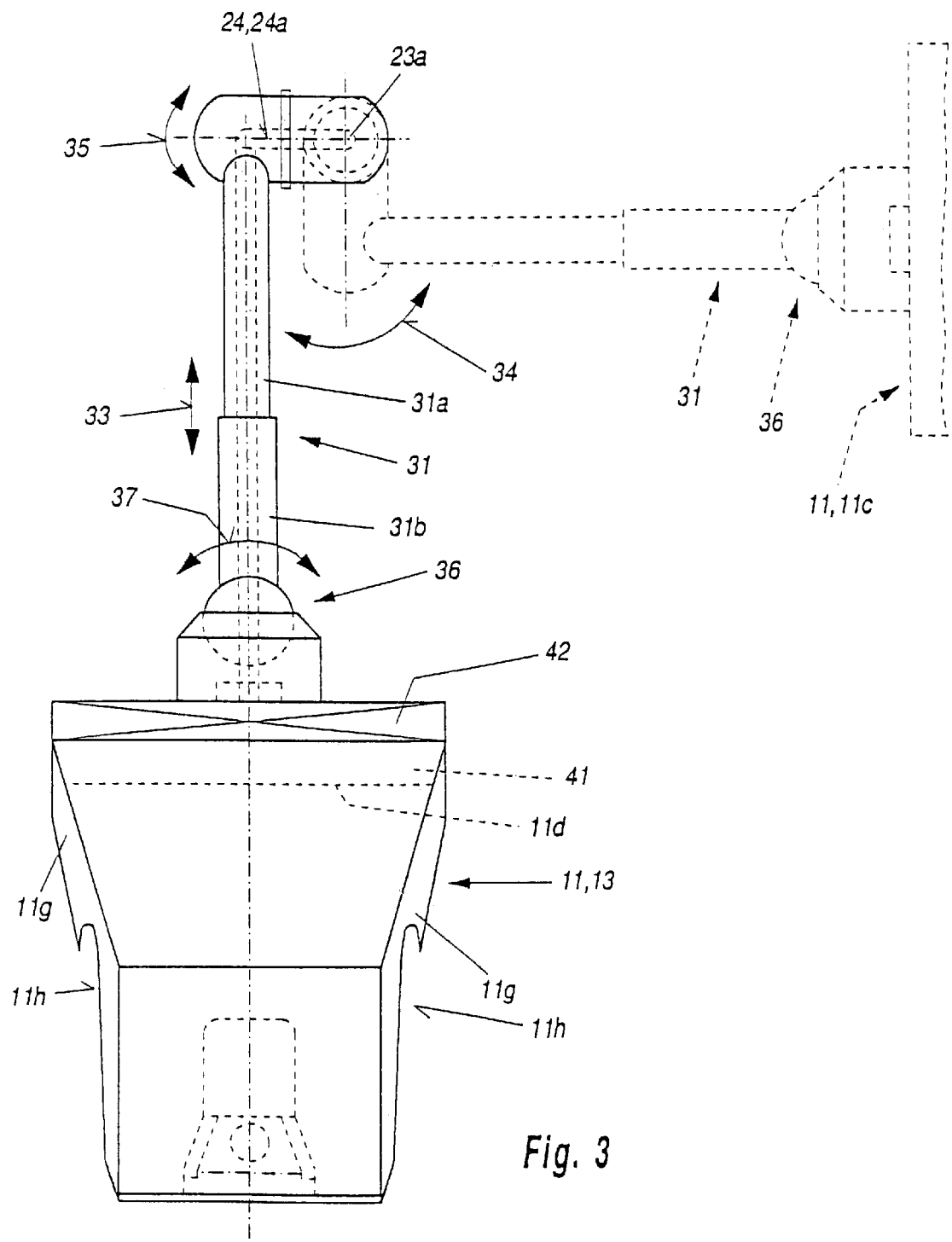
FIG. 3 the protection arrangement according to FIG. 2 in a perspective view from above and from the front.

The exemplary embodiment according to FIGS. 2 and 3, in which same or similar parts are provided with the same reference signs, differs from the above-described exemplary embodiment through a carrier arm 31 of modified configuration and, if applicable, also through a carrier device 15 which is formed lower or omitted. The latter can for example be realised in that the base joint 23 is arranged directly on the table plate 2 or on a small pedestal. The carrier arm 31 is a telescopic arm consisting of at least two carrier arm parts 31a, 31b which is selectively manually telescopable and may be fixable in its respective telescope disposition preferably by means of a non-illustrated fixing device. This degree of freedom is indicated by the double arrow 33. Further degrees of freedom are indicated by means of the double arrows 34, 35, namely the free pivotability around the vertical joint axis 23a and around the horizontal joint axis 24a of the joint 24, which can be formed between the rear telescope arm 31a and the upper joint part of the joint 23.

In the forward region of the carrier arm 31 is a particular joint in the form of a pivotable three-dimensional or ball joint 36 restricted in all directions, which joint makes possible a corresponding pivotability of the rearward protection arrangement part 11b which with the illustrated exemplary embodiment may be formed by means of a suction hood 13. The three-dimensional joint 36 may be arranged directly between the protection arrangement 11 and the carrier arm 31. With the present configuration there is arranged between the protection arrangement 11 and the carrier arm 31 the quick coupling 14a, whereby the three-dimensional joint 36 is arranged between the coupling part 14b associated with the carrier arm 31 and the forward carrier arm part 31b. Within the scope of the invention it is, however, also possible to arrange the three-dimensional joint 36 between the protection arrangement 11 and the quick coupling part 14c associated therewith, or between two other protection arrangement parts. The pivotability of the three-dimensional joint 36, restricted in all directions, is indicated by means of two double arrows 37, 38.

There may be arranged one or more media lines 39 externally on the carrier arm 31 or running longitudinally through the carrier arm 31, the latter being schematically illustrated by means of broken lines. In the case of running of the at least one media line 39 on the periphery of the carrier arm 31, this can be retained at the forward carrier arm 31b whereby the rear sections of the medium line extend exposed and upon telescoping of the forward carrier arm part 31b can follow freely.

FIG. 3 shows the carrier arm 31 in phantom with the protection arrangement 11 in a laterally rearwardly swivelled standby or parking position. Both in this position and also in its working position, the protection arrangement 11 may lay on the table plate 2. Insofar as there is desired a fixability of the protection arrangement 11 with regard to the carrier arm 31 or of the carrier arm 31 in the joint 24, there should be associated with the respective joint 24 a fixing device, which makes possible a fixing of the joint in the set position. This can for example be achieved by means of a stiffness of the joint concerned which is so great that manual displacement is possible but an unintended displacement is prevented. The latter applies also to the telescopability in particular, in upwardly swivelled oblique positions of the carrier arm 31 or in the case of a higher pedestal 32 in downwardly swivelled oblique positions, a self-sliding in or out of the carrier arm 31 is to be prevented. Also in this case, the fixing device can be provided by a stiffness of movement between the telescoping parts.

With the above-described exemplary embodiments, in those cases in which the protection arrangement 11 is formed as a suction hood 13, the work table 1 is described with a suction line 39a connected to the chamber of the suction hood 13 which line extends from the suction hood to a non-illustrated suction device in the region of the work table or to a central suction device to which the suction lines of a plurality of work tables can be connected. In these cases, there is associated with the individual suction device or the with the central suction device in each case a filter device having a filter 41 for the filtering of sucked up particles or contaminants.

With in the scope of the invention it is however also possible to arrange a filter 41, or a filter 41 and a suction device 42, on the suction hood in particular in its rear or upper region, as is shown in FIGS. 2 and 3. Herewith, there is arranged in the suction direction first the filter 41 and therebehind the suction device 42, e.g. a fan, in the rear or upper region of the suction hood. With this configuration the associated medium line does not fulfil the function of a suction line, rather that of a discharge line, for the discharged air sucked in the region of the suction hood.

With in the scope of the invention it is also possible to connect the discharge line to the suction hood, to a medium line port 39a next to the carrier arm 31, e.g. above by the carrier arm 31.

Figure 4:
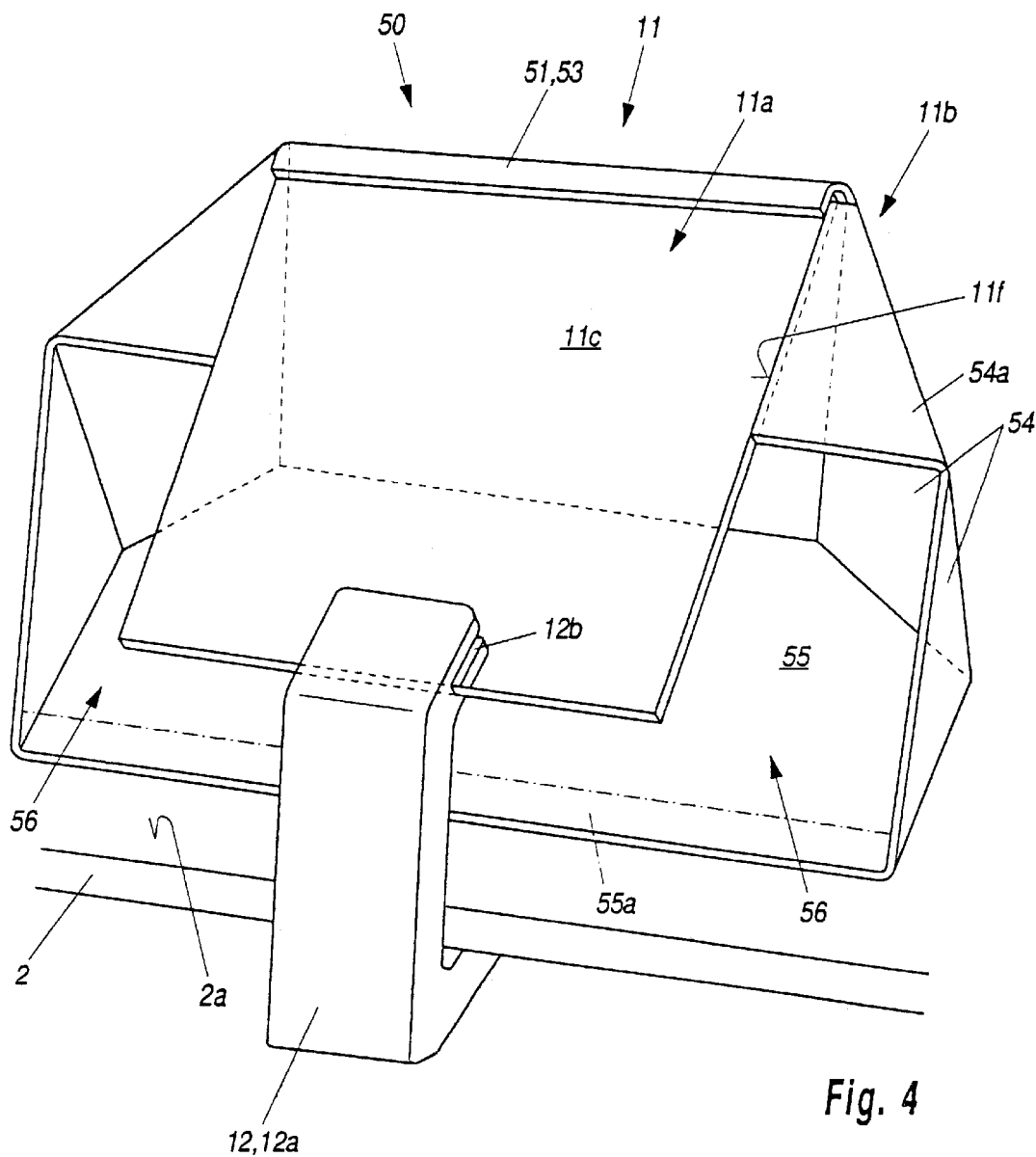
FIG. 4 a protection arrangement in accordance with the invention in a modified configuration, in a perspective front view from above.

With the exemplary embodiment according to FIGS. 4 to 6, with which the same or similar parts are provided with the same reference signs, the rearward protection arrangement part 11b is provided at its upper end with a suspension part 51 with which it is hung on the upper edge of the front plate 11c from the rear, forwardly or laterally engaging thereover. With the present configuration, the rearward protection arrangement part 11b has an approximately vertical rear wall 52 from the upper edge of which—at an acute angle which corresponds to the oblique position of the front plate 11c— an engaging limb 53 extends forwardly and downwardly. Side walls 54 may extend forwardly from the rear wall 52, here up to the front plate 11c, which side walls fill the wedge present between the rear wall 52 and the front plate 11c at least in the upper region. The spacing of the side walls 54 from one another is, with a slight play for movement, made wider than the front plate 11c so that the thus far described protection arrangement part 11b can be inserted onto the upper edge of the front plate 11c in the manner of a plug-in connection.

A floor wall 55 may extend forwardly from the lower edge of the rear wall 52, which floor wall is preferably connected with the side walls 54 in a protection box shape 50. For enlarging the capacity of the thus formed protection part or protection box, the rear wall 52 may develop obliquely or in particular in the lower region be rearwardly bulged outwardly. In comparable manner, the side walls 54 may also be laterally bulged outwardly at least in the lower region. If applicable, the cover wall sections 54a, serving for the lateral extension of the protection box 50, may be arranged in or parallel to the protection plate 11c. Sufficiently large access spaces 56 for the hands of the operating person to both sides of the holder 12 are thereby ensured in that the side walls 54 extend forwardly from the rear wall 52 only over a partial region of the protection plate 11c. The lateral bulges of the rear and side walls contribute to an enlargement of the access spaces 56 and to a ready access to the working position 9.

Due to the presence of the floor wall 55, this protection box forms a collection container for chips and dust, whereby the region of the work table lying rearwardly and also laterally of the working position is protected from contaminants in particular if this protection part is connected rearwardly or upwardly to a medium line or discharge line of a suction device. For the enlargement of the capacity of the protection box 50 there may be arranged at the forward edge of the floor wall 55 an up-standing front wall limb 55a. For the purpose of more rapid and ready installation and de-installation of the rearward protection arrangement part 11b it is advantageous to form the connection 39a for the medium or discharge line as a quick coupling.

Within the scope of the invention, the protection hood 13 and/or the protection part or the protection box 50 may be partially or completely of clear, transparent material, in particular of plastics, whereby preferably there may be involved an injection molded part manufactured in one piece.

Within the scope of the invention it is also possible to form the protection hood 13 or suction hood according to FIGS. 2 and 3 with a suspension part 51 and to suspend it on the upper edge region of the protection plate 11c, whereby the carrier arm 31 is no longer necessary.

What is claimed is:

1. A medical-technical or dental-technical work table (1) having a table surface, a protection arrangement (11) in a forward region of said table surface (2a), said protection arrangement (11) having a transparent protection plate (11c) arranged to extend upwardly and rearwardly obliquely, a holder (12) retaining said plate at a lower edge region in a self-supported manner on the work table (1), a rearward part (11b) of said protection arrangement being located behind the protection plate (11c), said rearward part (11b) of the protection arrangement being formed by a rear wall (11d), wherein said rear wall (11d) is stably supported and rests directly on the table surface of the work table (1), and an upper edge of the rear wall bears against but is not attached to the protection plate (11c) and jointly form said protection arrangement (11), and wherein the protection plate and the rear wall are each independent parts which are supported independently of each other.

2. A medical-technical or dental-technical work table (1) having a table surface, a protection arrangement (11) in a forward region of said table surface (2a), said protection arrangement (11) having a transparent protection plate (11c) arranged to extend upwardly and rearwardly obliquely, a holder (12) retaining said plate at a lower edge region thereof in a self-supported manner on the work table (1), a rearward part (11b) of said protection arrangement being located behind the protection plate (11c), said rearward part (11b) of the protection arrangement being held by a carrier arm, said rearward part (11b) of the protection arrangement being formed by a rear wall (11d), wherein an upper edge of said rear wall (11d) bears against but is not attached to the protection plate (11c) in a stable position and forms the protection arrangement (11) therewith, and wherein the protection plate and the rear wall are each independent parts which are supported independently of each other.

3. A medical-technical or dental-technical work table (1), which has a protection arrangement (13) connected with a carrier arm (31), said carrier arm being connected with the work table (1) in a rear region of said work table (1) by a base joint (23) so as to be able to pivot horizontally and vertically, wherein said carrier arm (31) is a telescopic arm comprising at least two carrier arm parts (31a, 31b), a ball joint (36) arranged between said protection arrangement and said carrier arm (31), in which ball joint the protection hood (13) is pivotally supported for rotation in all directions, and a chamber of the protection arrangement (13) being connected to a suction line (39a) extending from the protection arrangement (13) to a suction device, said suction line (39a) extending longitudinally through the carrier arm (31) and the ball joint.

4. A medical-technical or dental-technical work table according to 3, wherein the carrier arm (31) is positionable in a plurality of dispositions.

5. A medical-technical or dental-technical work table according to claim 3, wherein the protection arrangement (31) has a transparent front plate (11c).

6. A medical-technical or dental-technical work table according to claim 4 wherein the protection arrangement (31) has side walls (11g) and holes (11h) being located in a lower region of said side walls.

7. A medical-technical or dental-technical work table according to claim 3, wherein a filter (41) is arranged on the protection arrangement (13) in front of the suction line (39a).

8. A medical-technical or dental-technical work table according to claim 3, wherein said suction line (39a) extends outside along the carrier arm (31).

9. A medical-technical or dental-technical work table according to claim 3, wherein the protection arrangement (14) is releasably connected with the carrier arm (14) through a coupling (14a).

* * * * *